(12) United States Patent
Forster et al.

(10) Patent No.: US 11,813,426 B2
(45) Date of Patent: Nov. 14, 2023

(54) DRUG DELIVERY DEVICE INCLUDING SEAL MEMBER FOR NEEDLE OF SYRINGE

(71) Applicant: AMGEN INC., Thousand Oaks, CA (US)

(72) Inventors: Ronald Forster, Simi Valley, CA (US); Gregory Gordon, Moorpark, CA (US); Martin Hering, Camarillo, CA (US); Matthew Wayne Janke, Simi Valley, CA (US); Andrew N. King, Malvern, PA (US); Wael Mismar, Redondo Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 820 days.

(21) Appl. No.: 16/753,711

(22) PCT Filed: Oct. 1, 2018

(86) PCT No.: PCT/US2018/053685
§ 371 (c)(1),
(2) Date: Apr. 3, 2020

(87) PCT Pub. No.: WO2019/070552
PCT Pub. Date: Apr. 11, 2019

(65) Prior Publication Data
US 2020/0254172 A1 Aug. 13, 2020

Related U.S. Application Data

(60) Provisional application No. 62/569,242, filed on Oct. 6, 2017.

(51) Int. Cl.
*A61M 5/142* (2006.01)
*A61M 5/145* (2006.01)
(Continued)

(52) U.S. Cl.
CPC ...... *A61M 5/14248* (2013.01); *A61M 5/1456* (2013.01); *A61M 5/31571* (2013.01);
(Continued)

(58) Field of Classification Search
CPC ............ A61M 5/1456; A61M 5/14248; A61M 5/31571; A61M 2005/14256;
(Continued)

(56) References Cited

U.S. PATENT DOCUMENTS 5,114,400 A * 5/1992 Lynn .................. A61M 39/045
604/905
5,370,636 A * 12/1994 Von Witzleben ..... A61M 39/14
604/905
(Continued)

FOREIGN PATENT DOCUMENTS

CN 103007384 A 4/2013
CN 105682607 A 6/2016
(Continued)

OTHER PUBLICATIONS

International Search Report for International Application No. PCT/US2018/053685, dated Mar. 20, 2019.
(Continued)

*Primary Examiner* — James D Ponton
(74) *Attorney, Agent, or Firm* — MARSHALL, GERSTEIN & BORUN LLP

(57) ABSTRACT

Drug delivery devices and related methods of assembly are disclosed. The drug delivery device may include a housing, a container, a trigger member, and an interlock assembly. The trigger member may be selectively moveable relative to the housing to activate operation of at least one activatable element of the drug delivery device. The interlock assembly may include a lever mounted rotatably relative to the housing, a proximity sensor moveable between a first position
(Continued)

extending beyond an exterior surface of the housing and a second position retracted toward the housing, and a rotational biasing member operably connected to the proximity sensor via the lever. When the proximity sensor is in the first position, the interlock assembly may limit movement of the trigger member relative to the housing. The rotational biasing member may be configured to exert a torque biasing the proximity sensor toward the first sensor position.

11 Claims, 9 Drawing Sheets

(51) Int. Cl.
*A61M 5/315* (2006.01)
*A61M 5/158* (2006.01)

(52) U.S. Cl.
CPC .............. *A61M 2005/14256* (2013.01); *A61M 2005/14506* (2013.01); *A61M 2005/1585* (2013.01); *A61M 2005/3154* (2013.01); *A61M 2205/583* (2013.01)

(58) Field of Classification Search
CPC ........... A61M 2005/14506; A61M 2005/1585; A61M 2005/3154; A61M 2205/583; A61M 2005/14252; A61M 2005/1583; A61M 2005/2474; A61M 2205/13; A61M 2205/7536; A61M 5/1452; A61M 5/14566; A61M 5/3234; A61M 5/142
See application file for complete search history.

(56) References Cited

U.S. PATENT DOCUMENTS

| | | | | |
|---|---|---|---|---|
| 5,492,147 | A | * | 2/1996 | Challender ............. F16L 37/28 604/905 |
| 6,902,207 | B2 | * | 6/2005 | Lickliter ............... A61M 39/14 604/905 |
| 8,308,691 | B2 | | 11/2012 | Woehr et al. |
| 2003/0144633 | A1 | | 7/2003 | Kirchhofer |
| 2012/0010594 | A1 | | 1/2012 | Holt et al. |
| 2015/0128873 | A1 | | 5/2015 | Prescott et al. |
| 2016/0082189 | A1 | * | 3/2016 | Anderson ........... A61M 5/2033 604/174 |
| 2016/0106912 | A1 | | 4/2016 | Gross et al. |
| 2016/0175515 | A1 | * | 6/2016 | McCullough ........... A61M 5/20 604/65 |

FOREIGN PATENT DOCUMENTS

| | | | |
|---|---|---|---|
| WO | WO-9948546 A1 * | 9/1999 | ........ A61M 5/14216 |
| WO | WO-2016/145094 A2 | 9/2016 | |
| WO | WO-2017/139741 A1 | 8/2017 | |

OTHER PUBLICATIONS

Written Opinion of the International Searching Authority for International Application No. PCT/US2018/053685, dated Mar. 20, 2019.

Chinese Patent Application No. 2018800621183, First Office Action, dated Oct. 19, 2021.

* cited by examiner

DRUG DELIVERY DEVICE INCLUDING SEAL MEMBER FOR NEEDLE OF SYRINGE

CROSS-REFERENCE TO RELATED APPLICATION

This is the U.S. national phase of International Patent Application No. PCT/US2018/053685, filed Oct. 1, 2018, which claims priority to U.S. Provisional Patent Application No. 62/569,242, filed Oct. 6, 2017. The entire contents thereof of each of the foregoing are expressly incorporated herein by reference.

FIELD OF DISCLOSURE

The present disclosure generally relates to drug delivery devices and, more particularly, the configuration and assembly of a drug delivery device whose ability to be activated is dependent upon the state or position of a proximity sensor.

BACKGROUND

Automated or semi-automated drug delivery devices are sometimes used to inject a patient with a medicinal fluid or drug. These devices may replace manual drug delivery systems such as syringes, which require a patient or user to provide the motive force necessary to insert a needle or cannula into the patient's tissue and/or expel the drug from a container. Wearable or on-body injectors are one type of drug delivery device that may be used to automate the needle or cannula insertion process and/or the drug administration process. Certain patient groups or sub-groups, particularly those having limited dexterity and/or limited experience with self-injection, may benefit from the automation and/or simplification provided by wearable injectors and other drug delivery devices.

In some instances, the automated mechanisms of a drug delivery device may be activated prematurely. For example, a user or patient may inadvertently press an activation button prior to securement of the drug delivery device on the patient's skin. This may cause the drug delivery device to discharge the drug into the air, thereby resulting in the loss of the drug. Inadvertent activation is also possible during the shipping and/or handling of the drug delivery device prior to use.

Certain drug delivery devices incorporate a safety mechanism that limits drug delivery until a proximity sensor detects that the device has been placed against the patient's skin. Some such safety mechanisms require components having intricate geometries that can be difficult to construct and/or assemble. For instance, complex bending and feeding techniques may be needed to install a biasing element for biasing the proximity sensor to a locking position. Such complexities can increase costs and, in some cases, reduce reliability of the safety mechanism.

The present disclosure sets forth drug delivery devices and related methods of assembly embodying advantageous alternatives to existing drug delivery devices and methods of assembly, and that may address one or more of the challenges or needs mentioned herein, as well as provide other benefits and advantages.

SUMMARY

One aspect of the present disclosure provides a drug delivery device including a housing having an exterior surface releasably attachable to a patient, a container disposed at least partially within the housing, a trigger member, and an interlock assembly. The trigger member may be selectively moveable relative to the housing to activate operation of at least one activatable element of the drug delivery device. The interlock assembly may be configured to selectively limit movement of the trigger member relative to the housing. The interlock assembly may include a lever mounted rotatably relative to the housing, a proximity sensor, and a rotational biasing member operably connected to the proximity sensor via the lever. The proximity sensor may have a first sensor position wherein the proximity sensor extends beyond the exterior surface of the housing and a second sensor position wherein the proximity sensor is retracted toward the housing relative to the first sensor position. When the proximity sensor is in the first sensor position, the interlock assembly may limit movement of the trigger member relative to the housing. The rotational biasing member may be configured to exert a torque biasing the proximity sensor toward the first sensor position.

Another aspect of the present disclosure provides a method of assembling a drug delivery device. The method may include: (a) providing a lever having a first end and a second end, the first end of the lever being connected to a proximity sensor, at least one pivot rod extending outwardly from the second end of the lever; (b) mounting a rotational biasing member on the at least one pivot rod; (c) rotatably connecting the lever to a trigger member via the at least one pivot rod; and (d) connecting the trigger member to an interior surface of a housing of the drug delivery device.

An additional aspect of the present disclosure provides a drug delivery device including a housing having an exterior surface releasably attachable to a patient, a fluid conduit disposed in the housing, a syringe disposed in the housing, and a seal member connected to the syringe. The syringe may include a reservoir containing a drug, a needle, and a stopper. The needle may have a proximal end in fluid communication with the reservoir and a distal end disposed exterior to the reservoir. The stopper may movable through the reservoir from a proximal end of the reservoir toward a distal end of the reservoir to expel the drug from the reservoir via the needle during operation of the drug delivery device. The seal member may have: (i) an initial position wherein a distal end of the needle is partially disposed through the seal member, and (ii) a delivery position wherein the distal end of the needle is disposed through an exterior surface of the seal member into fluid communication with the fluid conduit.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

Figure 1:
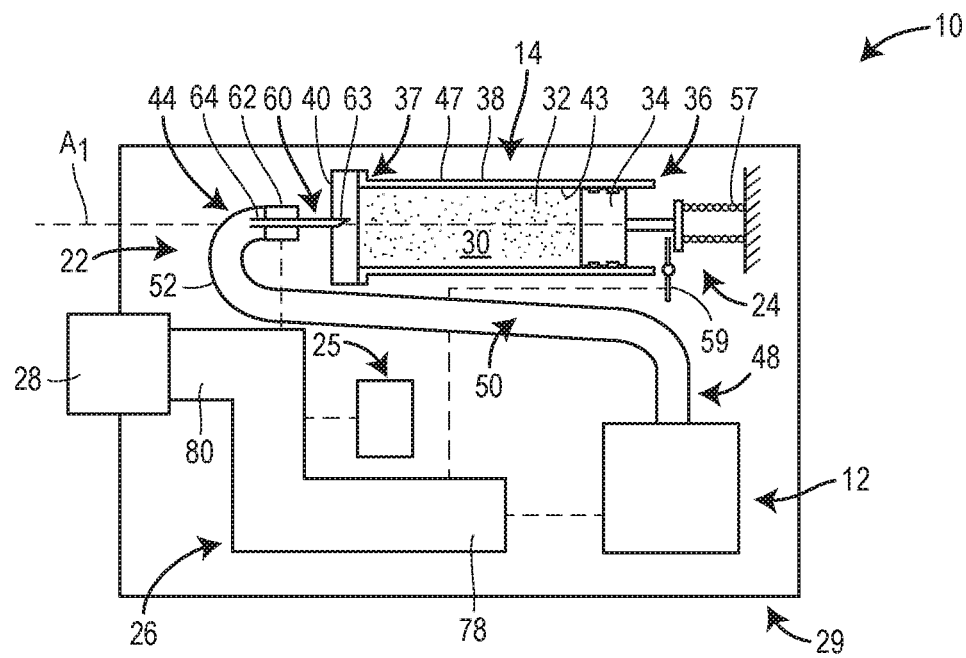
FIG. 1 is schematic top view of an embodiment of a drug delivery device in a pre-activation state in accordance with principles of the present disclosure.

The present disclosure generally relates to a drug delivery device including various systems for limiting delivery of a medicinal fluid or other drug product should the drug delivery device not be properly secured relative to a patient as determined by a proximity sensor. The drug delivery device may include various internal mechanisms and other activatable elements that, upon activation by a trigger member, facilitate or enact the automatic transfer of a drug from a container housed within the drug delivery device to the patient. Such activatable elements may include, but are not limited to, one or more of an insertion mechanism for inserting a needle and/or cannula into the patient, a fluid pathway connection mechanism for establishing fluid communication between the container and the insertion mechanism, and a drive mechanism for expelling the drug from the container, or any combination thereof. The trigger member may activate one or more of these activatable elements by sliding or otherwise moving relative to a housing of the drug delivery device in response to, for example, displacement of an external button by the patient or a user. An interlock assembly may be included to selectively limit movement of the trigger member relative to the housing based on a position of the proximity sensor. More particularly, the interlock assembly may prevent or inhibit movement of the trigger member when the proximity sensor extends or projects beyond an exterior surface of the housing, and may allow movement of the trigger member when the proximity sensor is retracted toward the housing as a result of the housing being pressed against the patient's skin. To reduce the possibility of premature activation of the drug delivery device, the proximity sensor may be normally arranged in its extended position. This is accomplished by a rotational biasing member which is operably connected to the proximity sensor via a lever and configured to exert a torque biasing the proximity sensor toward its extended position. The relative simplicity of this arrangement may advantageously improve or facilitate the manufacturability of the drug delivery device and may eliminate the need for a customized or intricately-designed biasing member for operating the proximity sensor, among other benefits and advantages.

Each of the foregoing components of the drug delivery device and methods of assembling such a device will now be described in more detail.

FIGS. 1-4 are schematic illustrations of an embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, which is releasably attachable to the patient's tissue 11 (e.g., the patient's skin). In other embodiments (not illustrated), the drug delivery device 10 may be configured as an autoinjector, such as an injection pen, which is temporarily held against the patient's tissue 11 over the course of an injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional, caregiver, or other user to administer the injection.

Generally, the drug delivery device 10 may include an insertion mechanism 12, a container 14, a fluid pathway connection mechanism 22, a drive mechanism 24, a controller 25, a trigger member 26, and an interlock assembly 70, each of which may be partially or entirely disposed within an interior space of a main housing 29. The trigger member 26 may be selectively moveable relative to the housing 28 to activate operation of one or more of the insertion mechanism 12, the fluid pathway connection mechanism 22, the drive mechanism 24, the controller 25, and other activatable element(s), or any combination thereof. In some embodiments, the trigger member 26 may be slidably connected to an interior surface 17 of the housing 29 via, for example, mating tabs and grooves. Additionally, in some embodiments, the trigger member 26 may be configured to move along a pre-defined linear path when actuated.

In order to activate the insertion mechanism 12, the fluid pathway connection mechanism 22, the drive mechanism 24, the controller 25, and/or other activatable element(s), the trigger member 26 may be operably connected to any one of, or any combination of, these elements, directly or indirectly, via mechanical means (e.g., a mechanical linkage or a gear assembly), electrical means, and/or electro-mechanical means. Dotted lines are used in FIGS. 1-4 to schematically illustrate the operational connection between the trigger member 26 and the insertion mechanism 12, the fluid pathway connection mechanism 22, the drive mechanism 24, and the controller 25. Regardless of the type of connection between the trigger member 26 and these activatable elements, movement of the trigger member 26 relative to the housing 29 in a certain direction(s) may provide the motive force necessary for activating one or more of the activatable elements.

An external button 28 may protrude through or otherwise be disposed at an exterior surface 19 of the housing 29 and may be manually displaceable by a patient or user. The external button 28 may be operably connected to the trigger member 26 such that displacement (e.g., linear displacement or depression) of the external button 28 causes joint translation of the external button 28 and the trigger member 26, when a proximity sensor 72 of the interlock assembly 70 is disposed in a second sensor position, as further described below. In some embodiments the external button 28 may be connected directly to or integrally formed with the trigger member 26; whereas, in other embodiments the external button 28 may be connected indirectly to the trigger member 26 via, for example, a mechanical linkage. In both of these cases, the user or patient may supply the motive force via the external button 28 necessary for activating one or more of the above-described activatable elements within the drug delivery device 10. In alternative embodiments, displacing or otherwise interacting with the external button 28 may transmit an electrical and/or mechanical signal to the controller 25, which in turn may execute programmable instructions to activate an internal actuator (e.g., an electric motor, a pneumatic or hydraulic pump, and/or a source of pressurized gas or liquid), which in turn may exert the motive force needed for moving the trigger member 26 to activate one or more of the insertion mechanism 12, the fluid pathway connection mechanism 22, and/or the drive mechanism 24. In such embodiments, the controller 25 may include a processor (e.g., a microprocessor) and a non-transitory memory for storing the programmable instructions to be executed by the processor.

Figure 2:
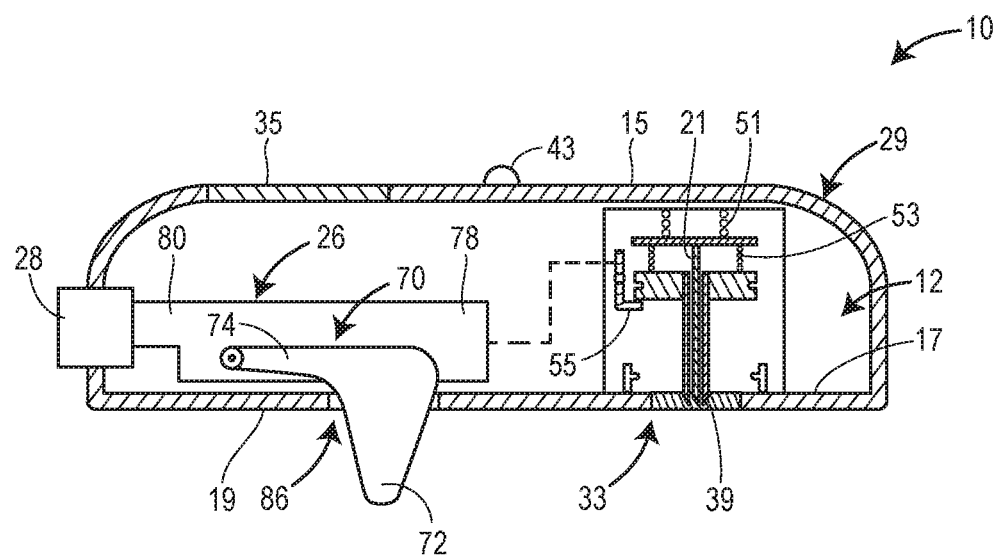
FIG. 2 is a schematic cross-sectional side view of the drug delivery device shown in FIG. 1 in the pre-activation state.
Figure 4:
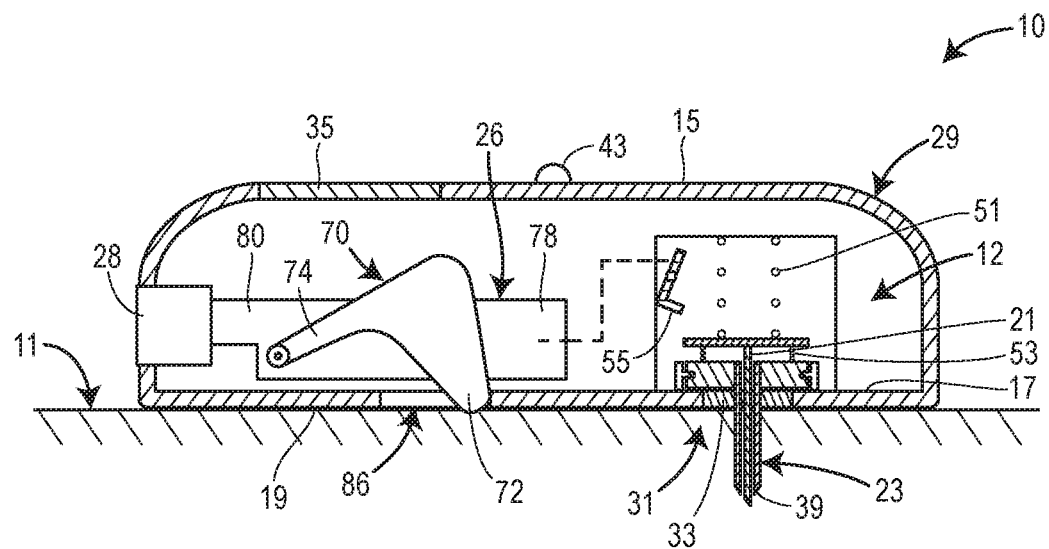
FIG. 4 is a schematic cross-sectional side view of the drug delivery device shown in FIG. 3 in the post-activation state.

Referring to FIGS. 2 and 4, the main housing 29 may include a wall 15 having an interior surface 17 and an exterior surface 19. The wall 15 may be a single unitary structure or made of multiple distinct structures interconnected with each other. The interior surface 17 of the wall 15 may define an interior space in which the insertion mechanism 12, the container 14, the fluid pathway connection mechanism 22, the drive mechanism 24, the controller 25, the trigger member 26 and/or other mechanisms and/or components may be disposed. In some embodiments, the interior space may be sealed shut to define an enclosed clean space possessing a sterile or aseptic internal atmosphere. The exterior surface 19 of a bottom portion of the wall 15 may be releasably attachable to the patient's tissue 11. In some embodiments, this may be accomplished with a skin adhesive applied to or otherwise disposed at the exterior surface 19 of the bottom portion of the wall 15 of the main housing 29. In some embodiments, the skin adhesive may be part of an adhesive patch attached to the exterior surface 19 of the bottom portion of the wall 15 of the main housing 29. The exterior surface 19 of a top portion of the wall 15 may include one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom portion of the wall 15, and optionally a pierceable sterile barrier 33, such as a pierceable septum, may extend across the opening 31 to seal the interior of the main housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the main housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu of adding a dark tint to the window 35 and/or shrinking the size of the window 35, advantageously protects the drug 35 from light in the visible range without substantially compromising the ability of the patient or user of the drug delivery device 10 to inspect the drug 32 within the container 14.

After the bottom portion of the wall 15 of the main housing 29 is attached to the patient's tissue 13 (e.g., the patient's skin), the insertion mechanism 12 may be activated by the trigger member 26 to move a subcutaneous delivery member from a retracted position, where a pointed distal end of the subcutaneous delivery member is withdrawn within the housing 29 (see FIG. 2), to a deployed position, where the pointed distal end projects from the housing 29 beyond the exterior surface 19 of the main housing 29 (see FIG. 4). In the present embodiment, this insertion sequence may involve the insertion mechanism 12 inserting a trocar 21 and a hollow cannula 23 surrounding the trocar 21 through the pierceable sterile barrier 33 and into the patient's tissue 11, as illustrated in FIG. 4. Immediately or shortly thereafter, the insertion mechanism 12 may automatically retract the trocar 21, leaving a distal end 39 of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or other polymer-based material. The relative flexibility of the cannula 23 may allow it to be disposed subcutaneously within the patient's tissue 11 for a period of a time without causing pain or significant discomfort to the patient. A distal end 39 of the cannula 23 may be sharpened to a point but may be more blunt than the distal end of the trocar 21. In alternative embodiments (not illustrated), the trocar 21 and cannula 23 may be omitted, and instead the insertion mechanism 12 may insert only a rigid, hollow needle into the patient's tissue 13 for subcutaneous delivery of the drug 32. Also, in any of the above-described embodiments, the subcutaneous delivery member may have a longitudinal axis that is perpendicular to or otherwise non-parallel to the longitudinal axis A1 of the container 14.

Still referring to FIGS. 2 and 4, in some embodiments the insertion mechanism 12 may include an insertion biasing member 51 and a retraction biasing member 53. Prior to activation of the insertion mechanism 12 by the trigger member 26, each of the insertion biasing member 51 and the retraction biasing member 53 may be retained in an energized state by a retaining member 55, as shown in FIG. 2. During activation, the trigger member 26 may translate, rotate, or otherwise move the retaining member 55 relative to the housing 29 such that the insertion biasing member 51 may be allowed to expand or otherwise release its stored energy, thereby moving the subcutaneous delivery member from the retracted position to the deployed position. In the illustrated embodiment, expansion of the insertion biasing member 51 causes the trocar 21 and the cannula 23 to move from the position seen in FIG. 2 where their distal ends are located within the housing 29, to the position shown in FIG. 4 where their distal ends are located outside of the housing 29. The retraction biasing member 53 may be retained in its energized state during the insertion procedure. Subsequent to the insertion procedure, the retraction biasing member 53 may release its stored energy and expand to move the trocar 21 from the deployed position back to the retracted position, leaving the cannula 23 in the deployed position.

In the illustrated embodiment, the insertion biasing member 51 and the retraction biasing member 53 are respective compression springs which are arranged concentrically with each other. Other power sources for the insertion biasing member 51 and/or the retraction biasing member 53 are also possible, including, for example, a torsion spring, an electric motor, a hydraulic or pneumatic pump, or a canister that releases a pressurized gas or a pressurized liquid to provide actuation energy. In some embodiments, the insertion biasing member 51 and the retraction biasing member 53 may be defined by a single electric motor which is operated in a forward direction and a reverse direction to provide the insertion and retraction movements. Also, in some embodiments, the retraction biasing member 53 may be omitted.

Referring back to FIG. 1, the container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the main housing 29 such that the container 14 can move relative to the main housing 29 during operation of the drug delivery device 10. The container 14 may have an elongate, barrel-like or cylindrical shape extending along a longitudinal axis A1. In embodiments where the drug delivery device 10 is configured as an on-body injector, the longitudinal axis A1 of the container 14 may be perpendicular or substantially perpendicular, or otherwise non-parallel, to a direction in which the insertion mechanism 12 inserts the subcutaneous delivery member such as the cannula 23 into the patient. This configuration may allow the on-body injector to have a generally planar, low-profile shape that can be worn by the patient without substantially impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14 to expel the drug 32 contained therein.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 30 may be completely or partially filled with the drug 32. The drug 32 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

With continued reference to FIG. 1, the drive mechanism 24 may be operably connected to the stopper 34 and to the trigger member 26. Upon activation by the trigger member 26, the drive mechanism 24 may be configured to move the stopper 24 along the longitudinal axis A1 through the reservoir 30 from the proximal end 36 of the container 14 to a distal end 37 of the container 14 in order to expel the drug 32 from the container 14. In some embodiments, the drive mechanism 24 may include a stopper biasing member 57 initially retained in an energized state by a retaining member 59, as shown in FIG. 1. During activation, the trigger member 26 may translate, rotate, or otherwise move the retaining member 59 relative to the housing 29 such that the stopper biasing member 57 may be allowed to expand or otherwise release its stored energy, thereby moving the stopper 24 through the reservoir 30 to expel the drug 32 contained therein (see FIG. 2). In alternative embodiments, the drive mechanism 24 may include a rotational power source (e.g., an electric motor), a gear module configured to convert the rotational speed and/or torque of the rotational movement output by the rotational power source, and/or a tether configured to restrain or otherwise regulate the expansion of the stopper biasing member.

Referring still to FIG. 1, an opening 45 may be formed in the wall 38 at the distal end 37 of the container 14. At least prior to operation of the drug delivery device 10, the opening 45 may be covered and sealed closed by a seal member 40, such as a pierceable septum, connected to the distal end 37 of the container 14. A proximal end surface of the seal member 40 and the interior surface 43 of the wall 38 of the container 14 may define the reservoir 30. Additionally, in some embodiments, a distal end surface of the stopper 34 may define the reservoir 30.

Generally, the seal member 40 may be configured to selectively permit access to the reservoir 30. During operation of the drug delivery device 10, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point at a proximal end 63 of a container access needle 60. In some embodiments, the seal member 40 may be clamped or otherwise secured to the distal end surface of the wall 38 of the container 14 by a fastener (e.g., a crimp ring) and/or adhered directly to the distal end surface of the wall 38 of the container 14.

Figure 3:
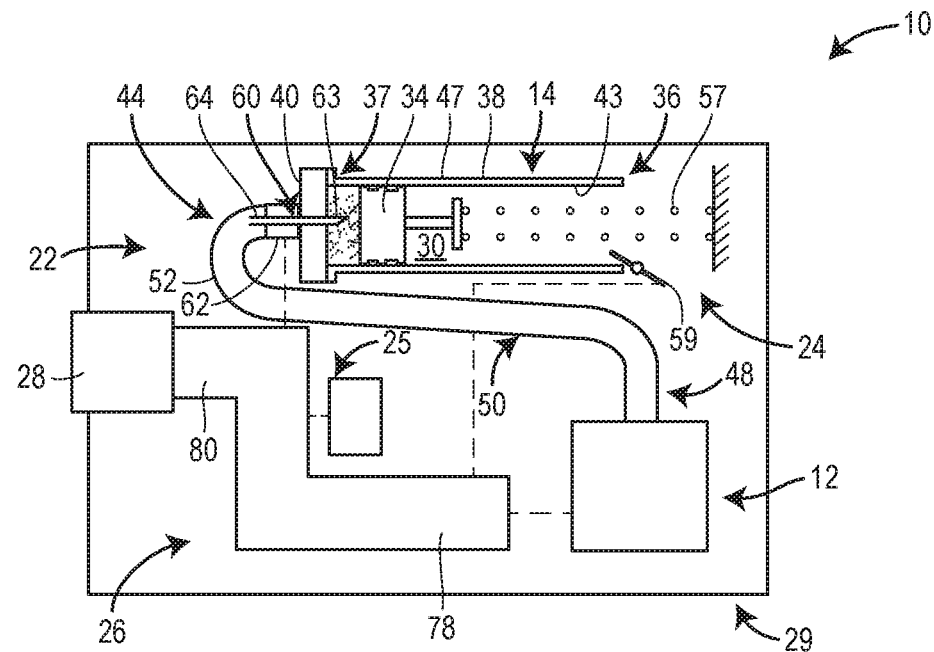
FIG. 3 is a schematic top view of the drug delivery device of FIG. 1 in a post-activation state.

Referring to FIGS. 1 and 3, the fluid pathway connection mechanism 22 may be configured to establish fluid communication between the container 14 and the insertion mechanism 12 via a sterile fluid flow path upon activation by the trigger member 26. Prior to activation of the fluid pathway connection mechanism 22, the container access needle 60 may be retained in a storage position wherein the proximal end 63 of the container access needle 60 is disposed exterior to, and thus not in fluid communication with, the reservoir 30 of the drug container 14 (see FIG. 1). During activation, the trigger member 26 may translate, rotate, or otherwise move the fluid pathway connection mechanism 22 relative to the housing 29 such that the fluid pathway connection mechanism 22 causes the container access needle 60 to move toward the reservoir 30 and into an operational position wherein the proximal end 63 of the container access needle 60 is in fluid communication with the reservoir 30 (see FIG. 3). Subsequently or simultaneously, the drive mechanism 24 may move the stopper 34 in the distal direction relative to the wall 38 of the container 14 to force the drug 32 stored in the container 14 through the container access needle 60, then through a sterile fluid flow path of the fluid pathway connection mechanism 22, and then into the cannula 23 or needle or other delivery member of the insertion mechanism 12 for subcutaneous delivery to the patient.

In some embodiments, a portion of or an entirety of the fluid pathway connection mechanism 22 may be slidably or moveably connected to the interior surface 17 of the wall 15 of the housing 29 such that at least a portion of the fluid pathway connection mechanism 22 can move relative to the housing 29 when pushed on by the trigger member 26. In such embodiments, the container 14 may be stationarily positioned or mounted relative to the housing 29 while the fluid pathway mechanism 22 is moved toward the container 14 during activation, causing the point 63 of the container access needle 60 to pierce through the seal member 40 and access the reservoir 30.

The fluid pathway connection mechanism 22 may include a first end 44 connected to the container access needle 60, a second end 48 connected to the insertion mechanism 12, and a fluid conduit 50 extending between the first end 44 and the second end 48. The fluid conduit 50 may be sterilized, and may be partially or entirely made of a flexible tubing 52. Initially, there may be slack in the flexible tubing 52 to allow the fluid pathway connection mechanism 22 to move relative to the housing 29 and/or to allow components of the insertion mechanism 12 to which the fluid pathway connection mechanism 22 is attached to move relative to the housing 29. In some embodiments, the fluid conduit 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

As shown in FIGS. 1 and 3, the first end 44 of the fluid pathway connection mechanism 22 may include a connection hub or mounting member 62. The mounting member 62 may cover a length of a distal end 64 of the container access needle 60 and connect the distal end 64 of the container access needle 60 to the flexible tubing 52. In some embodiments, the mounting member 62 may be mechanically connected, directly or indirectly, to the trigger member 26. Furthermore, during activation of the fluid pathway connection mechanism 22 by the trigger member 26, the trigger member 26 may translate, rotate, or otherwise move the mounting member 62 relative to the housing 29, thereby causing the container access needle 60 to move from its storage position (FIG. 1) to its operational position (FIG. 3).

More particularly with respect to the container access needle 60, it may possess a hollow, tubular shape with one or more openings at each of the proximal end 63 and the distal end 64. The container access needle 60 made be constructed of a rigid material including, but not limited to, metal (e.g., stainless steel) and/or plastic. In some embodiments, the mounting member 62 may be constructed of a different material than the container access needle 60 such that the mounting member 62 and the container access needle 60 are separate, but rigidly connected, components. In some embodiments, the mounting member 62 may be constructed of a rigid plastic material whereas the container access needle 60 may be constructed of metal. In other embodiments, the mounting member 62 and the container access needle 60 may be made of the same material such that they form a single, unitary one-piece structure.

In some embodiments, displacing the external button 28 and thereby moving the trigger member 26 may cause the simultaneous or substantially simultaneous activation of the insertion mechanism 12, the fluid pathway connection mechanism 22, the drive mechanism 24, the controller 25, and other activatable element(s) of the drug delivery device 10, or any combination thereof. In other embodiments, displacing the external button 28 and thereby moving the trigger member 26 may cause the insertion mechanism 12, the fluid pathway connection mechanism 22, the drive mechanism 24, the controller 25, and/or other activatable element(s) to activate in a predetermined sequential order.

With continued reference to FIGS. 1-4, and now additionally FIGS. 5-8, further description is provided with respect to the trigger member 26 and the interlock assembly 70. Generally, the interlock assembly 70 is configured to selectively limit movement of the trigger member 26 relative to the housing 29. Accordingly, the ability of the trigger member 26 to activate the insertion mechanism 12, the fluid pathway connection mechanism 22, the drive mechanism 24, the controller 25, and/or other activatable element(s) may depend upon the interlock assembly 70 having a locking configuration or an unlocking configuration. In the present embodiment, the interlock assembly 70 includes a proximity sensor 72, a lever 74, and a rotational biasing member 76; however, in other embodiments the interlock assembly 70 may include fewer or more components to achieve the locking and unlocking functionalities.

Prior to describing the interlock assembly 70 in detail, several aspects of the trigger member 26 will now be described in connection with FIGS. 5A-5C. The trigger member 26 may have an elongate shape generally extending along a longitudinal axis A2, and have a first longitudinal end 78 and a second longitudinal end 80. In the present embodiment, the trigger member 26 has an L-shape, which may allow the trigger member 26 to be nested within the housing 29 with other interior components and mechanisms. In some embodiments, the first longitudinal end 78 of the trigger member 26 may be operabaly connected, directly or indirectly, to the insertion mechanism 12 and/or the drive mechanism 24; whereas the second longitudinal end 80 may be operably connected, directly or indirectly, to the fluid pathway connection mechanism 22. In some embodiments, a mechanical linkage and/or gear assembly may connect the trigger member 22 to the insertion mechanism 12, the fluid pathway connection mechanism 22, and/or the drive mechanism 24. Such a mechanical linkage and/or gear assembly may be configured to convert the linear motion of the trigger member 26 in one direction into linear or rotational motion in a different direction for activating the insertion mechanism 12, the fluid pathway connection mechanism 22, the drive mechanism 24, and/or other activatable elements.

In some embodiments, the external button 28 may be rigidly connected to or mounted on the second longitudinal end 80 of the trigger member 26. In other embodiments, the second longitudinal end 80 of the trigger member 26 may itself constitute the external button 28.

The trigger member 26 may be slidably connected to the interior surface 17 of the housing 29 such that the trigger member 26, in response to displacement of the external button 28, moves along a pre-defined linear path that is parallel or substantially parallel to the longitudinal axis A2 of the trigger member 26. This slideable connection may be achieved via mating tabs and grooves disposed on the trigger member 26 and the interior surface 17 of the housing 29, and/or by a track-like member disposed on the interior surface 17 of the housing 29.

Figure 5A:
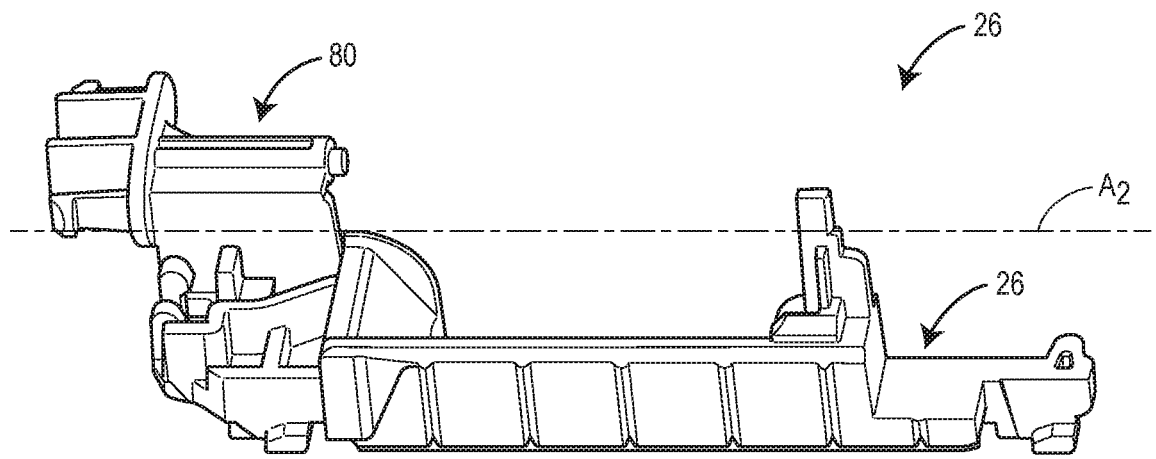
FIGS. 5A and 5B are top perspective views, from different angles, of a trigger member in accordance with principles of the present disclosure.
Figure 5B:
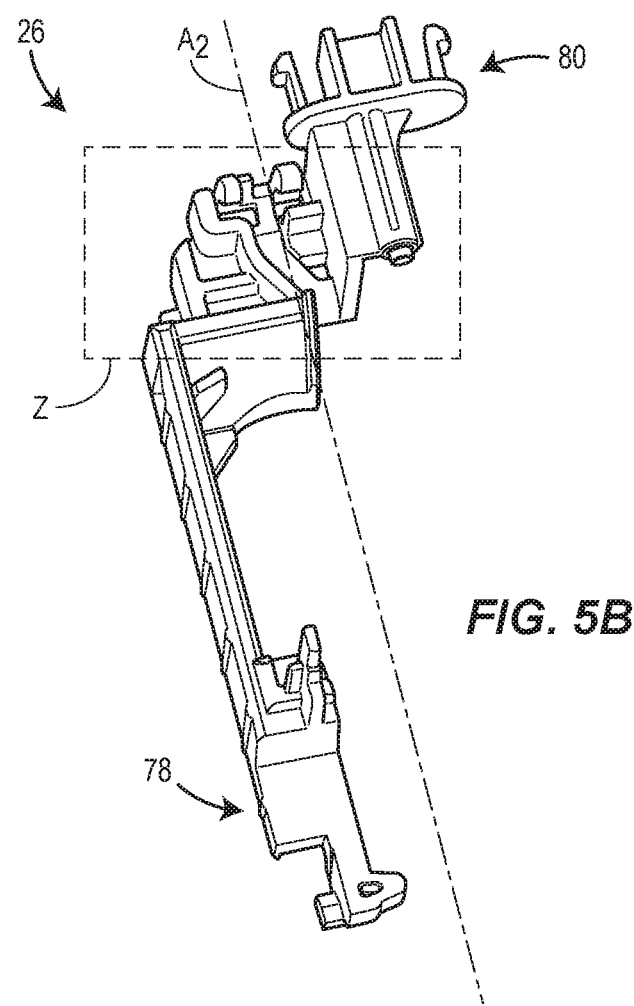
Figure 5C:
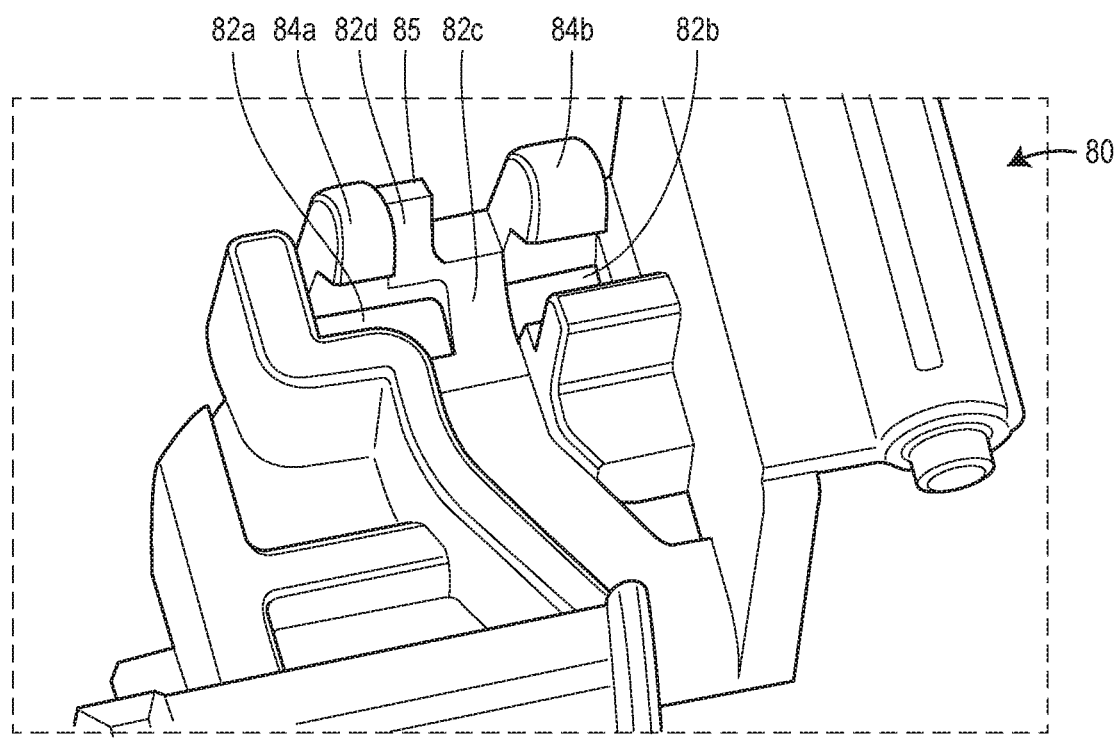
FIG. 5C is an enlarged view of section Z in FIG. 5B.

Still referring to FIGS. 5A-5C, the second longitudinal end 80 of the trigger member 26 may include several recesses 82a, 82b, 82c, and 82d for receiving and/or securing various components associated with the interlock assembly 70. As used herein, the term "recess" refers to any portion of a wall that is set back with respect to an adjacent portion of the wall and encompasses a groove, a slot, a depression, a through hole, a blind hole, a nest, and the like. In the illustrated embodiment, the recesses 82a and 82b are defined, at least in part, by respective vertically-upstanding hook members 84a and 84b formed at the second longitudinal end 80 of the trigger member 26. The recess 82c may be formed in an upwardly facing surface of a bottom wall of the trigger member 26 and may be positioned between the recess 82a and the recess 82b. The recess 82d may be defined, at least in part, by a vertically-upstanding tab member 85 and may also be positioned between the recess 82a and the recess 82b. As shown in FIG. 5C, the recesses 82a, 82b, 82c, and 82d are immediately adjacent to each other, thereby effectively forming a single continuous recess. However, in alternative embodiments, some or all of the recesses 82a, 82b, 82c, and/or 82d may be separated from each other by an intervening wall(s) and therefore may be distinct from each other.

Figure 6A:
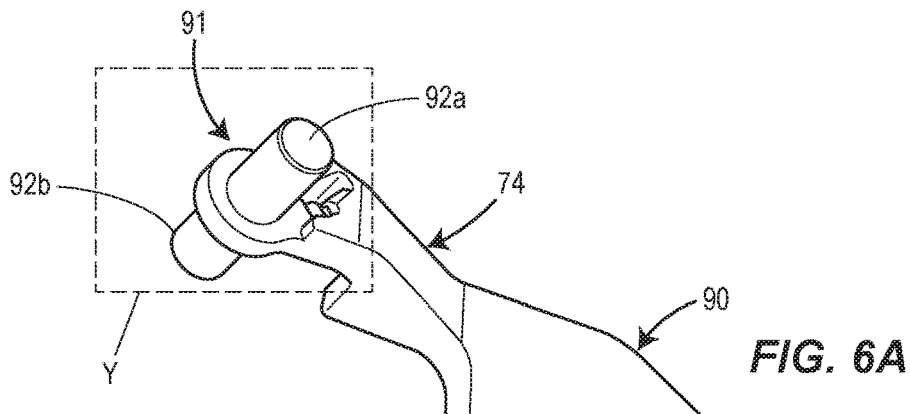
FIGS. 6A and 6B are perspective views, from opposite sides, of a lever and a proximity sensor in accordance with principles of the present disclosure.
Figure 6B:
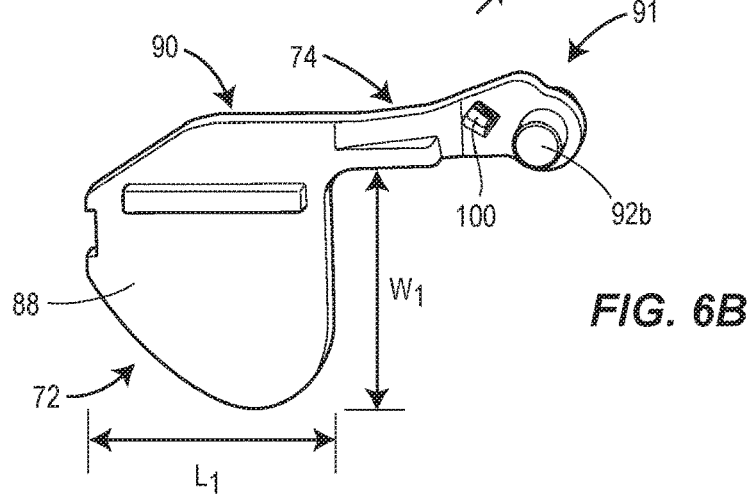
Figure 6C:
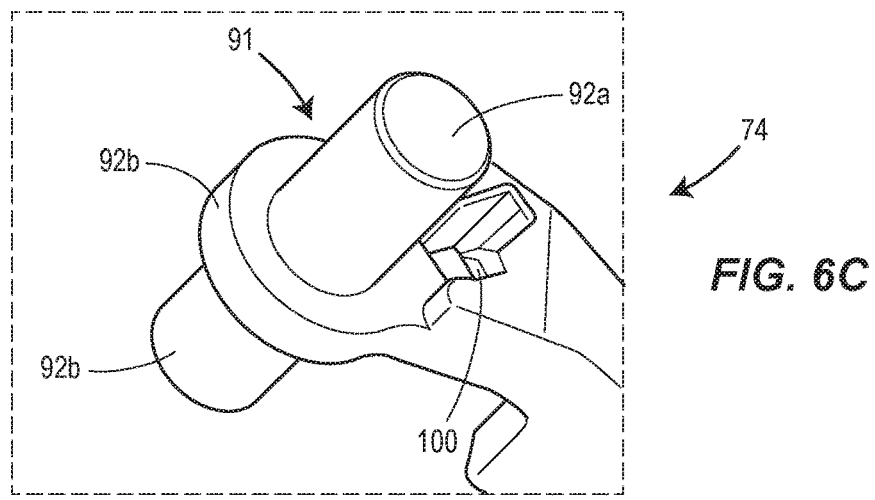
FIG. 6C is an enlarged view of section Y in FIG. 6A.

Turning to FIGS. 6A-6C, illustrated are several views of the proximity sensor 72 and the lever 74. In the illustrated embodiment, the proximity sensor 72 and the lever 74 are a single, integrally-constructed unitary structure. However, in other embodiments, the proximity sensor 72 and the lever 74 may be separate distinct structures that are rigidly connected to each other. Generally, the lever 74 may be mounted rotatably relative to the housing 29 and may rotate about the rotational axis A3. The proximity sensor 72 may jointly rotate together with the lever 74 about the rotational axis A3. Rotation of the proximity sensor 72 about rotational axis A3 may allow the proximity sensor 72 to move between a first sensor position or state (see FIG. 2) wherein the proximity sensor 72 extends from the housing 29 beyond the exterior surface 19 of the housing 29 and a second sensor position or state (see FIG. 4) wherein the proximity sensor 72 is retracted toward the housing 29 relative to the first sensor position or state. To facilitate this movement of the proximity sensor 72, an opening 86 may extend between the interior surface 17 and the exterior surface 19 of the bottom portion of the wall 15 of the housing 29, as illustrated in FIGS. 2 and 4. In some embodiments, the opening 86 may take the form of an elongated slot, having a length which is substantially greater than a width of the slot. Such an elongated slot may be generally rectangular in shape, in some embodiments. Also, in some embodiments, such as the one illustrated in FIG. 4, in the second sensor position the entire proximity sensor 72 may be retracted through the opening 86 into the housing 29.

In embodiments where the interior space of the main housing 29 is manufactured to define a sterile or aseptic internal environment, a sealing member such as a septum may cover the opening 86 and permit the proximity sensor 72 to slidably penetrate therethrough. The sealing member may sealingly engage the outer surface of the proximity sensor 72 and the rim of the opening 86 so as to inhibit or prevent the ingress of contaminants through any gaps between the proximity sensor 72 and the rim of the opening 86. In other embodiments, this sealing member may be omitted.

The first sensing position of the proximity sensor 72 may correspond to when the drug delivery device 10 is not properly secured relative to the patient for an injection; whereas the second sensing position of the proximity sensor 72 may correspond to when the drug delivery device 10 is properly secured relative to the patient for an injection. In the first sensing position, the proximity sensor 72 may be configured to limit or prevent movement of the trigger member 26 relative to housing 29 along the above-described pre-defined path. Thus, the trigger member 26 may be unable to activate one or more of the activatable elements such as the insertion mechanism 12, the fluid pathway connection mechanism 22, the drive mechanism 24, and/or the controller 25. This ability of the proximity sensor 72 in the first sensor position to limit movement of the trigger member 26 may be a result of a front end of the proximity sensor 72 abutting a portion of the housing 29 adjacent the opening 86 through which the proximity sensor 72 extends in the first sensor position. Accordingly, in a general sense, the bottom portion of the wall 15 of the housing 29 may define a stop member for the proximity sensor 72 and/or the trigger member 26 when the proximity sensor 72 is in the first sensor position.

As depicted in FIG. 4, when the exterior surface 19 of the bottom portion of the wall 15 of the housing 19 is releasably attached to the patient's tissue 11, thus rending the drug delivery device 10 ready for injection, the patient's tissue 11 may push the proximity sensor 72 from the first sensing position to the second sensor position. In the second sensing position, the proximity sensor 72 may permit movement of the trigger member 26 relative to housing 29 along the above-mentioned pre-defined path. Thus, the trigger member 26 may be allowed to activate one or more of the activatable elements such as the insertion mechanism 12, the fluid pathway connection mechanism 22, the drive mechanism 24, and/or the controller 25.

As shown in FIGS. 6A and 6B, the proximity sensor 72 may include a generally planar wall or plate 88 which extends in a downward direction from the lever 74 when installed within the drug delivery device 10. A bottom edge of the plate 88 may be curved or rounded so as to not cause injury or discomfort to the patient. As illustrated in FIGS. 6A and 6B, the plate 88 may a thickness T1 that is substantially less than a length L1 and a width W1 of the plate 88 so that the plate 88 may fit through the elongated, slot-like shape of the opening 86. The proximity sensor 72 may be arranged such that the length L1 of the plate 88 is parallel or substantially parallel to the longitudinal axis A2 of the trigger member 26 and/or the pre-defined linear path of movement of the trigger member 26. This configuration may render the proximity sensor 72 more resistant to bending and/or other physical deformations should the user or patient apply a significantly large force to the external button 28 in an attempt to overcome the lock provided by the proximity sensor 72 when the proximity sensor 72 is arranged in the first sensor position.

Figure 7A:
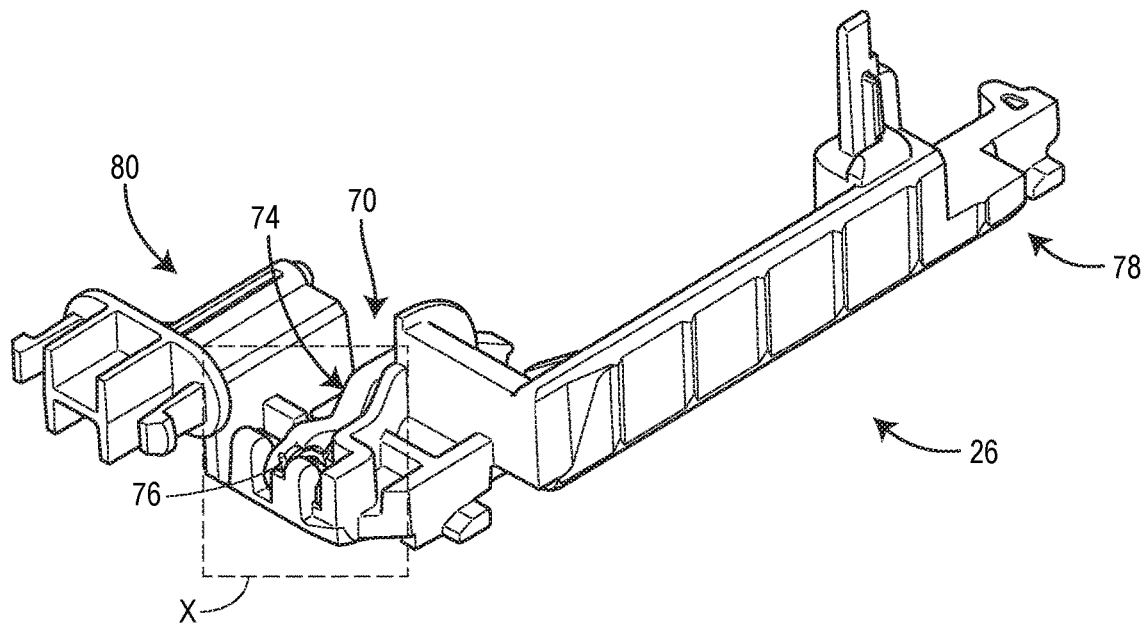
FIGS. 7A and 7B are perspective views, from opposite sides, of an assembled arrangement of a interlock assembly and a trigger member in accordance with principles of the present disclosure, with a proximity sensor arranged in a first sensor position.
Figure 7B:
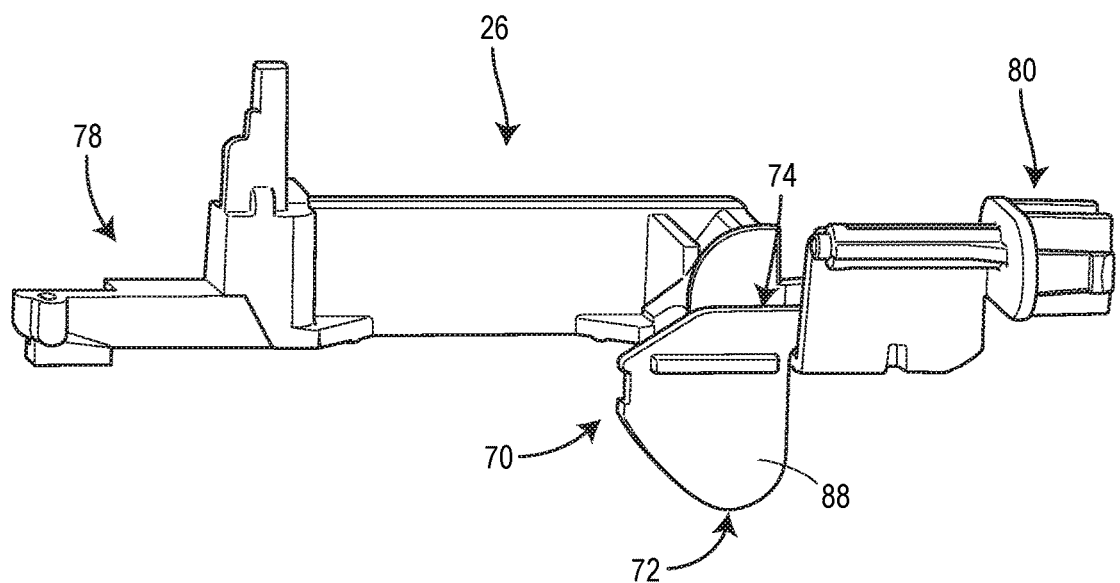
Figure 7C:
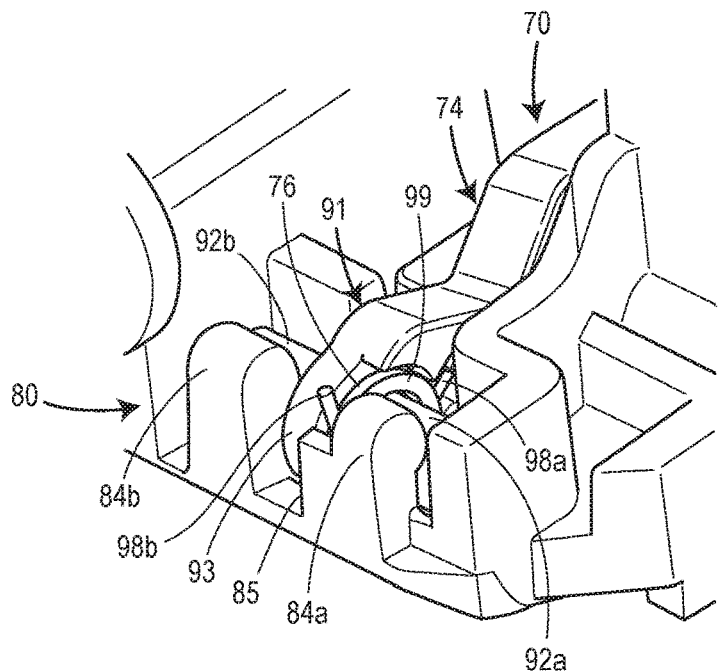
FIG. 7C is an enlarged view of section X in FIG. 7A.

Referring still to FIGS. 6A-6C, the lever 74 may possess a first longitudinal end 90 and a second longitudinal end 91. The first longitudinal end 90 of the lever 74 may be integrally formed with or otherwise rigidly connected to the proximity sensor 72. The second longitudinal end 91 of the lever 74 may be rotatably connected to the second longitudinal end 80 of the trigger member 26 such that the lever 74 is configured to rotate relative to the trigger member 26 about the rotational axis A3. The rotatable or hinge-like connection between the lever 74 and the trigger member 26 may be enabled by a first pivot rod 92a and a second pivot rod 92b which extend from opposite lateral sides of the second longitudinal end 90 of the lever 74 and which are received in, respectively, the recess 82a and the recess 82b formed in the second longitudinal end 80 of the trigger member 26 (see FIGS. 7A and 7C). Each of the first and second pivot rods 92a and 92b may be generally cylindrical in shape, which may allow them to smoothly rotate within their respective recesses 82a and 82b. The rotational axis A3 may be defined by and pass centrally through each of the first and second pivot rods 92a and 92b. Furthermore, the first and second pivot rods 92a and 92b when seated in their respective recesses 82a and 82b may each be arranged perpendicular, substantially perpendicular, or otherwise non-parallel to the longitudinal axis A2 of the trigger member 26. Accordingly, the rotational axis A3 may also be perpendicular, substantially perpendicular, or otherwise non-parallel to the longitudinal axis A2 of the trigger member 26. Also, as shown in FIGS. 7A and 7C, which is a center portion 93 of the second longitudinal end 91 of the lever 74, positioned between the first and second pivot rods 92a and 92b, may be received within the recess 82c formed in the second longitudinal end 80. The center portion 93 may include a circular or otherwise curved circumferential surface allowing it to rotate smoothly within the recess 82c. In a general sense, the connection between the second longitudinal end 91 of the lever 74 and the second longitudinal end 80 of the trigger member 26 may define a hinge which allows the proximity sensor 72 to rotate relative to the housing 29. Also, it is noted that alternative constructions of the lever 74 may omit one or both of the first and second pivot rods 92a and 92b.

As a result of seating the first pivot rod 92a, the second pivot rod 92b, and the center portion 93 of the lever 74, respectively, in the recesses 82a, 82b, and 82c formed in the trigger member 26, the lever 74 (and the remainder of the interlock assembly 70) may jointly translate together with the trigger member 26 when the trigger member 26 is translated relative to the housing 29 along its pre-defined linear path during activation. Accordingly, the rotational axis A3 of the lever 74 may also translate relative to the housing 29 during activation movement of the trigger member 26.

Referring to FIGS. 6B and 6C, a recess 100 may be formed in the second longitudinal end 91 of the lever 74. As described below in more detail, the recess 100 may be configured to receive an end of the rotational biasing member 76. The recess 100 may be positioned between the first pivot rod 92a and the first longitudinal end 90 of the lever 74. Furthermore, the recess 100 may be accessible in a direction generally traveling away from the first pivot rod 92a.

Figure 8:
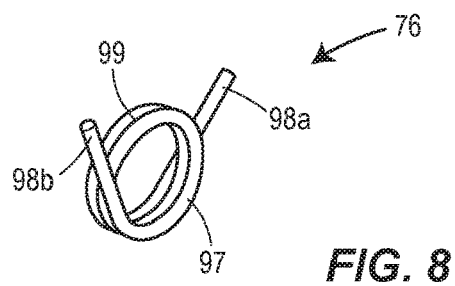
FIG. 8 is a perspective view of a rotational biasing member in accordance with principles of the present disclosure.

Regarding the rotational biasing member 76, in some embodiments, it may be constructed as a helical torsion spring, as shown in FIG. 8. The helical torsion spring may include a coil 97 having a first end or tail 98a, a second end or tail 98b, and a helically-wound center portion 99 arranged between and connecting the first and second ends 98a and 98b. As illustrated in FIG. 8, the helically-wound center portion 99 of the coil 97 may define a central opening of the rotational biasing member 76. Furthermore, as shown in FIG. 8, the first end 98a of the coil 97 may be linear or otherwise possess less curvature than the helically-wound center portion 99 of the coil 97. Similarly, the second end 98b of the coil 97 may be linear or otherwise possess less curvature than the helically-wound center portion 99 of the coil 97.

Figure 7D:
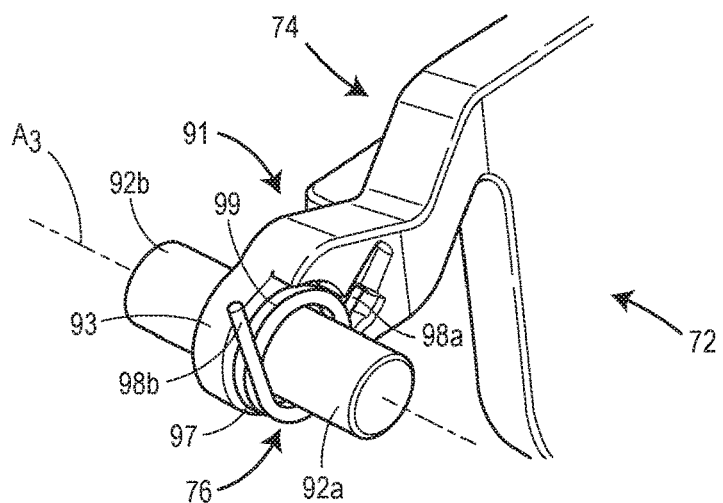
FIG. 7D illustrates the same view as FIG. 7C, but with the trigger member being omitted.

The rotational biasing member 76 may be mounted on the lever 74 such that the rotational biasing member 76 is configured to exert a torque, via the lever 74, that biases the proximity sensor 72 toward the first sensor position. In the present embodiment, this may be accomplished by mounting or wrapping the helically-wound center portion 99 of the rotational biasing member 76 around the first pivot rod 92a of the lever 74, positioning the first end or tail 98a of the rotational biasing member 76 in the recess 100 formed in the second longitudinal end 80 the second longitudinal end 91 of the lever 74, and positioning the second end or tail 98b of the rotational biasing member 76 in the recess 82d formed in the second longitudinal end 80 of the trigger member 26, as seen in FIGS. 7C and 7D. Such an arrangement may allow the rotational biasing member 76 to push off of the trigger member 26 and thereby exert a torque on the lever 74, which in turn exerts a torque biasing the proximity sensor 72 toward the first sensor position. By placing the exterior surface 19 of a bottom portion of the wall 15 against the patient's tissue 11, the user or patient may provide the force or torque necessary to overcome the biasing torque of the rotational biasing member 76, thereby causing the proximity sensor 72 to move from the second sensor position to the first sensor position.

While the rotational biasing member 76 of the present embodiment is configured as a helical torsion spring, alternative embodiments of the rotational biasing member 76 may be configured differently, for example, as a spiral torsion spring or any other suitable biasing member that can exert a torque biasing the proximity sensor 72 toward the second sensor position.

A method of using the drug delivery device 10 to deliver a drug or other medicinal fluid to a patient will now be described with reference to FIGS. 1-4. Initially, the patient or user may remove the drug delivery device 10 from any primary or secondary packaging in which the drug delivery device 10 was shipped or sold by a manufacturer or other producer. In some embodiments, the container 14 may be pre-filled with the drug 32 and pre-loaded into the housing 29 by the manufacturer or producer so that the patient or user is not required to perform these tasks. At this stage, the proximity sensor 72 may be arranged in the first sensor position as a result of the biasing torque provided by the rotational biasing member 76, as seen in FIG. 2. As such, the proximity sensor 72 may limit or prevent movement of the trigger member 26 relative to the housing 29. Therefore, should the user or patient, or anyone or anything else, apply an activating force to the external button 28, the proximity sensor 72 will abut the housing 29 and thereby prevent the trigger member 26 from moving and activating any of the activatable elements of the drug delivery device 10. Accordingly, the position of the trigger member 26 may be locked relative to the housing 29 when the proximity sensor 22 is in the first sensor position.

Next, the patient or user may releasably attach the exterior surface 19 of the bottom portion of the wall 15 of the housing 29 to the patient. This may involve the patient or user pressing or otherwise disposing the exterior surface 19 of the bottom portion of the wall 15 against the patient's tissue 11 (e.g., the patient's skin). In embodiments where an adhesive is applied to the exterior surface 19 of the bottom portion of the wall 15 of the housing 29, the adhesive may be responsible for temporarily attaching the exterior surface 19 of the housing 29 to the patient. As a preliminary step, the patient or user may remove a removable liner covering the adhesive from the housing 19 to expose the adhesive. Disposing the exterior surface 19 of the housing 29 against the patient's tissue 11 may cause the patient's tissue 11 to contact bottom end of the proximity sensor 72 and push the proximity sensor 72 against the biasing torque of the rotational biasing member 76. This, in turn, may causes the proximity sensor 72 to retract partially or entirely within the opening 86 formed in the housing 29, and thereby move from the first sensor position (FIG. 2) to the second sensor position (FIG. 4). In the second sensor position, the proximity sensor 72 may no longer limit movement of the trigger member 26 relative to the housing 29. Thus, the trigger member 26 may be free to move relative to the housing 29 in response to displacement of the external button 28 by the patient or user. Stated another way, the trigger member 26 may be unlocked when the proximity sensor 72 is arranged in the second sensor position.

Next, the user or patient may manually displace (e.g., depress) the external button 28 to activate one or more of the activatable elements of the drug delivery device 10. The trigger member 26, as well as the interlock assembly 70, may move jointly together with the external button 28 when the external button 28 is displaced. In some embodiments, this movement may be linear or translational movement. As described above, the movement of the trigger member 26 relative to the housing 29 may cause the trigger member 26 to, directly or indirectly, contact or otherwise interact with one or more of the insertion mechanism 12, the fluid pathway connection mechanism 22, the drive mechanism 24, the controller 25, or other activatable element(s), or any combination thereof. In some embodiments, the movement of the trigger member 26 when the external button 28 is displacement may cause the trigger member 26 to simultaneously or substantially simultaneously activate at least each of the insertion mechanism 12, the fluid pathway connection mechanism 22, and the drive mechanism 24. Accordingly, the insertion mechanism 12 may move the delivery member (e.g., the cannula 23) from the retracted position to the deployed position, the fluid pathway connection mechanism 22 may move the container access needle 60 from the storage position to the operational position, and the drive mechanism 24 may move the stopper 34 through the reservoir 30 to expel the drug 32 from the reservoir 30 through the container access needle 60, then through the fluid pathway connection mechanism 22, then through the needle insertion mechanism 12, and finally out through the delivery member (e.g., the cannula 23) and into the patient.

Subsequently, the patient or user may detach or remove the drug delivery device 10 from their body. In some embodiments, this may result in the rotational biasing member 76 pushing or deploying the proximity sensor 72 out through the opening 86 in the housing 29, such that the proximity sensor 72 moves from the second sensor position to the first sensor position. Accordingly, the proximity sensor 72 may once again lock the position of the trigger member 26 relative to the housing 29. In such embodiments, the drug delivery device 10 may include a biasing member such as a spring to exert a force biasing the trigger member 26 and/or external button 28 toward a home position corresponding to where the trigger member 26 and/or external button 28 are positioned prior to activation by the patient or user.

In alternative embodiments, the above-described method of using the delivery device 10 may include fewer or more steps, depending on the type of treatment regimen in which the drug delivery device 10 is being used.

Methods of assembling the drug delivery device 10 will now be described, with reference to FIGS. 1-8. As an initial step, the container 14, which may be pre-filled with the drug 32, may be installed within the housing 29. Also, other components of the drug delivery device 10, such as the insertion mechanism 12, the fluid pathway connection mechanism 22, the drive mechanism 24, and/or the controller 25, also may be installed within the housing 29 at this initial stage. The installation of these components may involve mounting or otherwise connecting these components to the interior surface 17 of the housing 29. In alternative embodiments, one or more of these components may be installed within the housing 29 after the trigger member 26 and/or the interlock assembly 70 has been installed within the housing 29.

With regard to assembling the interlock assembly 70, initially the rotational biasing member 70 may be inspected for any defects. Next, the rotational biasing member 70 may be placed with other rotational biasing members in a feeder bowl of an automated assembly machine. Subsequently, this machine or a worker may mount or otherwise connect the rotational biasing member 70 to the lever 74. In the present embodiment, this step may involve inserting the first pivot rod 92a through the central opening of the rotational biasing member 70 such that the helically-wound center portion 99 of the rotational biasing member 76 extends around the first pivot rod 92a. While mounting the helically-wound center portion 99 on the first pivot rod 92a, the first end or tail 98a of the rotational biasing member 76 may be inserted into and/or secured within the recess 100 formed in the second longitudinal end 91 of the lever 74. In some embodiments, this insertion process may involve rotating the rotational biasing member 70 around the first pivot rod 92a until the first end or tail 98a is generally aligned with the recess 100 and subsequently snapping the first end or tail 98a over a ridge on the second longitudinal end 91 of the lever 74 and into the recess 100.

Next, the assembled arrangement of the lever 74 and the rotational biasing member 76 (which may constitute the interlock assembly 70) may be rotatably connected to the trigger member 26. The trigger member 26 may or may not be connected to the interior surface 17 of the housing 29 during this step. This rotatable connection may be achieved by lowering the assembled arrangement of the lever 74 and the rotational biasing member 76 generally from above into the second longitudinal end 80 of the trigger member 26, such that: the first pivot rod 92a of the lever 74 is inserted into and/or secured within the recess 82a in the trigger member 26, the second pivot rod 92b of the lever 74 is inserted into and/or secured within the recess 82b of the trigger member 26, the center portion 93 of the lever 74 is inserted into and/or secured within the recess 82c of the trigger member 26, and the second end or tail 98b of the rotational biasing member 76 is inserted into and/or secured within recess 82d of the trigger member 26. In some embodiments, the this step may involve snapping one or more of the first pivot rod 92a, the second pivot rod 92, and/or the second end or tail 98b over a ridge formed on the trigger member 26 and into its respective recess 82a, 82b, or 82d. This top-down assembly of the interlock assembly 70 into the trigger member 26 advantageously may facilitate a more streamlined manufacturing process.

In embodiments where the trigger member 26 and the interlock assembly 70 are connected to each other outside of the main housing 29, the trigger member 26 subsequently may be lowered into the main housing 29 such that the proximity sensor 72 of the interlock assembly 70 may be inserted through the opening 86 formed in the bottom portion of the wall 15 of the housing 29, while the trigger member 26 is simultaneously slidably connected to the interior surface 17 of the bottom portion of the wall 15 of the housing 29. Alternatively, in embodiments where the trigger member 26 has been previously installed in the housing 29, the proximity sensor 72 may be inserted through the opening 86 formed in the bottom portion of the wall 15 of the housing 29 as the lever 74 is rotatably connected to the trigger member 26 in the manner described above.

With regard to connecting the trigger member 26 to the interior surface 17 of the housing 29, in some embodiments this process may involve snapping a protrusion or tab formed on the trigger member 26 into a generally linear groove or slot formed on the interior surface 17 of the housing 29, or vice versa. Accordingly, the trigger member 26 may be configured to, when not locked by the interlocking assembly 70, slide along a linear pre-defined or predetermined path relative to the housing 29.

Subsequently, if it has not been done already, the trigger member 26 may be operably connected to one or more of the activatable elements within the housing 29, including, but not limited to, the insertion mechanism 12, the fluid pathway connection mechanism 22, the drive mechanism 24, and/or the controller 25. This may involve connecting the trigger member 26 indirectly (e.g., via a mechanical or electromechanical linkage) or directly to the one or more activatable elements. The external button 28 may be rigidly connected to the second longitudinal end 80 of the trigger member 26 after the trigger member 26 has been installed in the housing 29.

As a final step, any openings in the housing 29 may be sealed or otherwise closed shut, thereby enclosing the pre-filled container 14, the trigger member 26, the interlock assembly 70, the insertion mechanism 12, the fluid pathway connection mechanism 22, the drive mechanism 24, the controller 25, and any other internal elements of the drug delivery device 10 within the housing 29. At the completion of the assembly process, the drug delivery device 10 may be configured as a pre-loaded and pre-filled drug delivery device.

In each of the foregoing embodiments, the container of the drug delivery device is configured as an ampoule or vial that is penetrated by an external container access needle upon activation of the device. However, alternative embodiments of the drug delivery device may include a container possessing an integrated or staked needle, such as a syringe (e.g., a pre-filled syringe). FIGS. 9A-10B illustrate one such alternative embodiment of the drug delivery device. Elements of the drug delivery device 110 depicted in FIGS. 9A-10B which are the same as or similar to those shown in FIGS. 1-8 are designated by the same reference numeral, incremented by 100. A description of many of these elements is abbreviated or even eliminated in the interest of brevity.

Referring to FIGS. 9A-10B, the container 114 is configured as a syringe including a reservoir 130 filled with a drug 132, a stopper 134 moveably disposed in the reservoir 130, and a rigidly mounted container needle 210 having a proximal end 212 in fluid communication with the reservoir 130 and a distal end 214 disposed exterior to the reservoir 130. A proximal end 136 of a wall 138 of the container 114 may define a barrel 216, and a distal end 137 of the wall 138 of the container 114 may define a neck 218. A diameter, width, and/or cross-section of the neck 218 may be smaller than a diameter, width, and/or cross-section of the barrel 216. Furthermore, a diameter, width, and/or cross-section of the neck 218 may taper in a direction moving away from the barrel 216. The barrel 216 may surround an entirety of or a portion of the reservoir 130. A portion of the reservoir 130 may also be surrounded by the neck 218. Furthermore, a portion of the needle 210 may extend through and be surrounded by the neck 218. The needle 210 may be staked, adhered, or otherwise rigidly connected to the portion of the wall 138 defining the neck 218 such that the needle 210 is prevented from moving relative to the wall 138 of the container 114. In this way, the wall 138 of the container 144 may function as a mounting structure for the needle 210. In some embodiments, the distal end 214 of the needle 210 may terminate at a sharpened point or tip 226.

The volume of the drug 132 contained in the reservoir 130 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 130 may be completely or partially filled with the drug 132. The drug 132 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

Figure 9A:
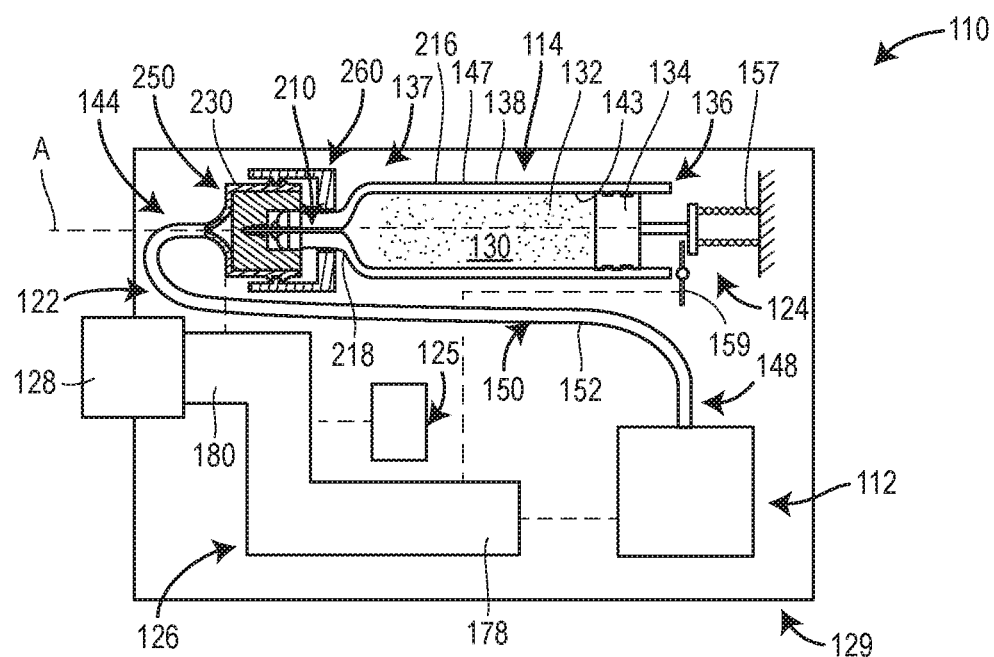
FIG. 9A is a schematic top view of another embodiment of a drug delivery device in a pre-activation or initial state in accordance with principles of the present disclosure.
Figure 9B:
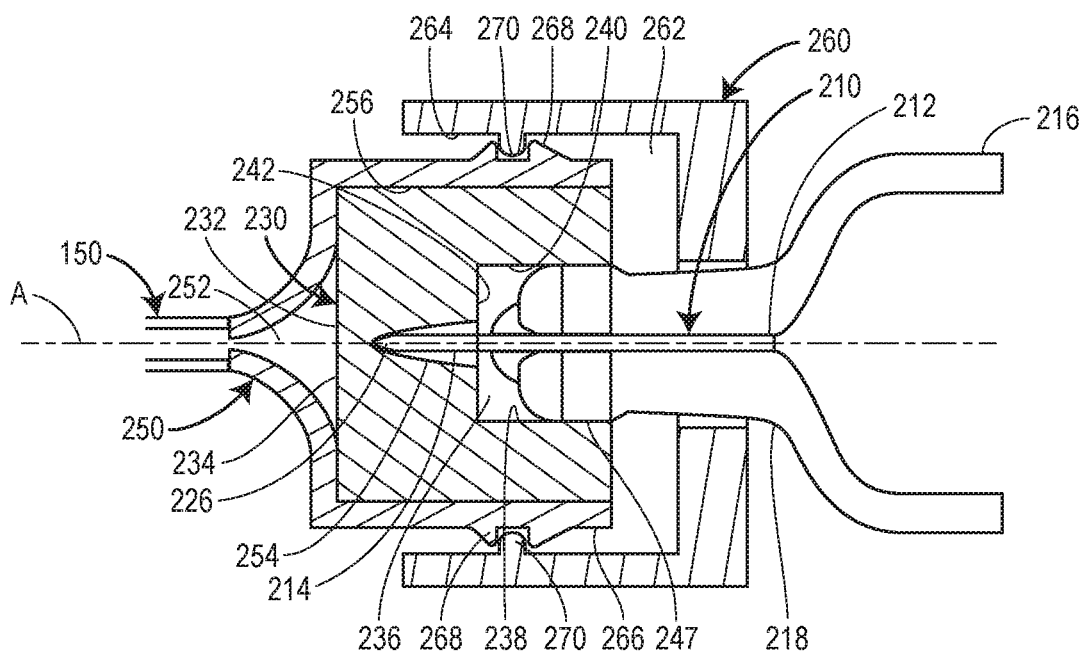
FIG. 9B is enlarged cross-sectional view of a syringe and a seal member depicted in FIG. 9A.
Figure 10A:
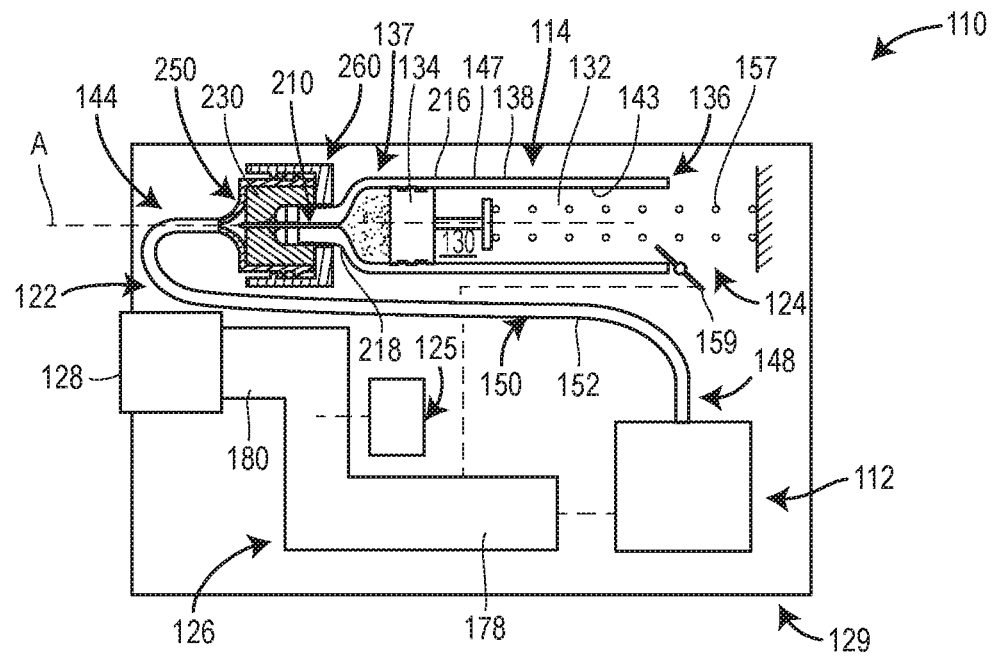
FIG. 10A is a schematic top view of the drug delivery device of FIG. 9A in a post-activation or delivery state.
Figure 10B:
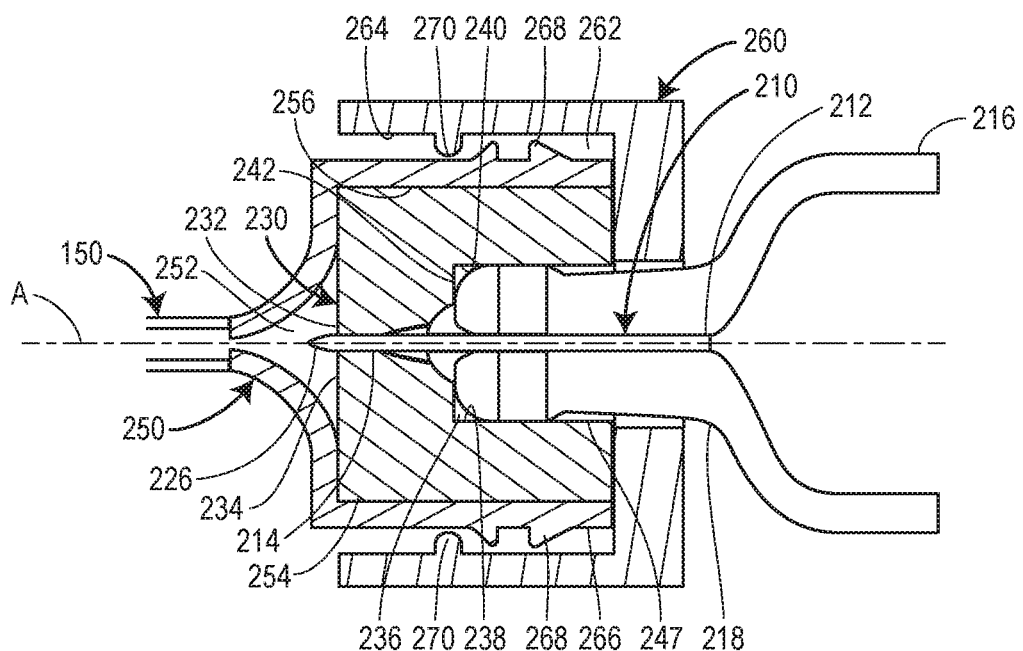
FIG. 10B is enlarged cross-sectional view of the syringe and the seal member depicted in FIG. 10A.

In order to keep the distal end 214 of the needle 210 aseptic or sterile prior to activation of the drug delivery device 210, the distal end 214 of the needle 210 may be disposed at least partially through a seal member 230 in an initial or storage position or state, as shown in FIGS. 9A and 9B. The seal member 230 may be mounted such that it is moveable relative to the container 114. During activation of the drug delivery device 210, the trigger member 26 may cause the seal member 230 to move in a proximal direction toward the distal end 37 of the container 114, or cause the container 114 to move in the distal direction toward the seal member 230, such that the tip 226 of the distal end 214 of the needle 210 penetrates or otherwise is disposed entirely through a distally facing portion 232 of an exterior surface 234 of the seal member 230, as shown in FIGS. 10A and 10B. The seal member 230 may be referred to as being in a delivery or operational position or state when the distal end 214 of the needle 210 is disposed through the distally facing portion 232 of the exterior surface 234 of the seal member 230. In this exposed position, the distal end 214 of the needle 210 may be in fluid communication with the fluid conduit 150 of the fluid pathway connection mechanism 122, such that the drug 132 can be expelled from the reservoir 130 by the stopper 134, then into the needle 210, then into the fluid conduit 150, and subsequently into the patient via the cannula 23.

As shown in FIG. 9B, a recess 236 may be formed in a proximal end of the seal member 230 for slidably receiving an end portion of the neck 218 of the container 114. A radially inwardly facing portion 238 of an interior surface 240 of the seal member 230 may surround the recess 236. The radially inwardly facing portion 238 of the interior surface 240 may sealingly and slidably engage an exterior surface 247 of the neck 218. Accordingly, the interface between the neck 218 and the seal member 230 may provide a sterile barrier that inhibits or prevents the ingress of contaminants into the recess 236. When the needle 230 is arranged in the initial position, the neck 218 may be partially inserted into the recess 236 such that the neck 218 is spaced apart from a proximally facing portion 242 of the interior surface 240 of the seal member 230, as illustrated in FIG. 9B. When the needle 230 is arranged in the delivery position, the gap between the neck 218 and the proximally facing portion 242 of the interior surface 240 of the seal member 230 may be decreased, or eliminated such that the neck 218 engages the proximally facing portion 242 of the interior surface 240 of the seal member 230, as shown in FIG. 10B.

The seal member 230 may be made, partially or entirely, of a flexible or elastically deformable material such as rubber, for example, which is capable of being penetrated or pierced by the sharpened point 226 of the distal end 214 of the needle 210. Additionally, in some embodiments, the material used to construct the seal member 230 may be permeable to any one of or any combination of the gaseous sterilizing agents chosen from the following non-exclusive list of gaseous sterilizing agents: ethylene oxide (EtO), ozone, chlorine dioxide, nitrogen dioxide, and steam (e.g., pressurized water vapor). In some embodiments, the material used to construct the seal member 230 may be a rubber material that is permeable to EtO. The seal member 230 may be subjected to a gaseous sterilization treatment after the neck 218 of the container 114 has been tightly inserted into the recess 236. By constructing the seal member 230 of a material that is permeable to a gaseous sterilizing agent, less exposure time may be needed for sterilizing the interior surface 240 of the seal member 230, the distal end 214 of the needle 210, and/or the space or gap between the neck 218 of the container 114 and the proximally facing portion 242 of the interior surface 240 of the seal member 230 with the gaseous sterilization agent. This is because the gaseous sterilizing agent may be able to diffuse through the seal member 230 to reach the interior surface 240.

In some embodiments, the sharpened point 226 of the distal end 214 of the needle 210 may be embedded within the material of the seal member 230 when the needle 210 is arranged in the initial position. In other embodiments, the sharpened point 226 of the distal end 214 of the needle 210 may be disposed in the empty space of the recess 236 when the needle 210 is arranged in the initial position.

Referring to FIGS. 9B and 10B, the seal member 230 may be connected to the fluid conduit 150 via a first connection hub 250. The first connection hub 250 may have an annular or sleeve like shape defining a hollow interior 252. An interior surface 254 of the first connection hub 250 may surround the hollow interior 252. The seal member 230 may be inserted or otherwise received within the hollow interior 252 of the first connection hub 250 such that a radially outwardly facing portion 256 of the exterior surface 234 of the seal member 230 sealingly engages the interior surface 254 of the first connection hub 250. Accordingly, the interface between the seal member 230 and the first connection hub 250 may provide a sterile barrier that inhibits or prevents the ingress of contaminants into the hollow interior 252 of the first connection hub 250. In some embodiments, the first connection hub 250 may be configured to receive the seal member 230 via press-fit or interference-fit connection. Furthermore, in some embodiments, the first connection hub 250 may be constructed of a more rigid and/or less permeable material than the seal member 230.

While a proximal end of the first connection hub 250 may be rigidly connected to the seal member 230, a distal end of the first connection hub 250 may be rigidly connected to the fluid conduit 150. This connection may be achieved via any suitable means, including fasteners, adhesives, or a press-fit or interference-fit connection. The distal end of the first connection hub 250 may have a reduced diameter and/or cross-section relative to the proximal end of the first connection hub 250 so that the distal end of the first connection hub 250 is suitable for interfacing with the relatively small diameter of the fluid conduit 150. An interior of the fluid conduit 150 may always be in communication with the hollow interior 252 of the first connection hub 250. When the needle 210 is arranged in the delivery position, the distal end 214 of the needle 210 may be disposed in the hollow interior 252 of the first connection hub 250 and/or within the interior of the fluid conduit 150, and therefore can discharge the drug 132 into the fluid conduit 150.

As shown in FIGS. 9A and 10A, the first connection hub 250 may be operably connected to the trigger member 126 such that the first connection hub 250 moves in the proximal direction towards the container 114 in response to activating movement of the trigger member 126. In some embodiments, the first connection hub 250 may be mechanically connected, directly or indirectly, to the trigger member 126. The tight fit between the first connection hub 250 and the seal member 230 causes the seal member 230 to move jointly together with the first connection hub 250 in the proximal direction towards the container 114. Because the needle 210 of the container 114 is held stationary relative to the housing 129 of the drug delivery device 110, the proximal movement of the seal member 230 may cause the distal end 214 of the needle 210 to penetrate through the exterior surface 234 of the seal member 230 and into fluid communication with the fluid conduit 150, as shown in FIGS. 10A and 10B.

To prevent or inhibit movement of the first connection hub 250 relative to the container 114 prior to activation of the drug delivery device 110, a second connection hub 260 may be included. In general, the second connection hub 260 may frictionally engage the first connection hub 250 to limit movement of the first connection hub 250 relative to the container 114 and/or the second connection hub 260. The second connection hub 260 may be rigidly connected to the container 114 in order to perform this function. As shown in FIGS. 9B and 10B, the second connection hub 260 may have an annular or sleeve like shape defining a hollow interior 262. An interior surface 264 of the second connection hub 260 may surround the hollow interior 262. The first connection hub 250 may be inserted or otherwise received within the hollow interior 262 of the second connection hub 260. At least a portion of the interior surface 264 of the second connection hub 260 may frictionally engage an exterior surface 266 of the first connection hub 250. The frictional force between the first connection hub 250 and the second connection hub 260 may be overcome by the motive force provided by the trigger member 126 upon activation of the drug delivery device 110. In some embodiments, as shown in FIGS. 9B, the frictional connection may be achieved via a first gripping element 268 disposed on the exterior surface 266 of the first connection hub 250 and which engages (e.g., matingly engages) a second gripping element 270 disposed on the interior surface 264 of the second connection hub 260. In the present embodiment, the first gripping element 268 is a recess, and the second gripping element 270 is a protrusion dimensioned to tightly fit within the recess. In alternative embodiments, the first gripping element 268 may be a protrusion and the second gripping element 270 may be recess.

In terms of manufacturing or assembling the drug delivery device 110, the process may be similar to that described above in connection with the drug delivery device 10.

Where appropriate, any of the above-described sub-assemblies, mechanisms, components, features, functionalities, methods of assembly or manufacture, methods of use, and other aspects of the drug delivery devices 10 and 110 may be replaced with and/or combined with any of the sub-assemblies, mechanisms, components, features, functionalities, methods of manufacture or assembly, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; U.S. Provisional Patent Application No. 62/535,777 entitled "GAS PERMEABLE SEALING MEMBER FOR DRUG CONTAINER AND METHODS OF ASSEMBLY"; U.S. Provisional Patent Application No. 62/536,909 entitled "DRUG DELIVERY DEVICE WITH CONTAINER ACCESS SYSTEM AND RELATED METHOD OF ASSEMBLY"; U.S. Provisional Patent Application No. 62/536,911 entitled "DRUG DELIVERY DEVICE WITH GEAR MODULE AND RELATED METHOD OF ASSEMBLY"; U.S. Provisional Patent Application No. 62/547,500 entitled "WEARABLE INJECTOR WITH STERILE ADHESIVE PATCH"; U.S. Provisional Patent Application No. 62/548,750 entitled "NEEDLE INSERTION MECHANISM FOR DRUG DELIVERY DEVICE"; International Patent Application No. PCT/US2017/017627 entitled "DRUG DELIVERY DEVICE, METHOD OF MANUFACTURE, AND METHOD OF USE"; International Patent Application No. PCT/US2017/026524 entitled "DRUG DELIVERY DEVICE, METHOD OF MANUFACTURE, AND METHOD OF USE"; International Patent Application Publication No. WO/2016/130679 entitled "ROTATIONALLY BIASED INSERTION MECHANISM FORA DRUG DELIVERY PUMP"; International Patent Application Publication No. WO/2016/141082 entitled "DEVICE AND METHOD FOR MAKING ASEPTIC CONNECTIONS"; and International Patent Application Publication No. WO/2016/145094 entitled "DRIVE MECHANISMS FOR DRUG DELIVERY PUMPS".

Drug Information

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number 2 as set forth therein in FIG. 2 and/or the heavy chain of sequence identification number 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers 305-351, including TN8-19-1 through TN8-19-40, TN8-19 con1 and TN8-19 con2; peptibodies of the mL2 family of sequence identification numbers 357-383; the mL15 family of sequence identification numbers 384-409; the mL17 family of sequence identification numbers 410-438; the mL20 family of sequence identification numbers 439-446; the mL21 family of sequence identification numbers 447-452; the mL24 family of sequence identification numbers 453-454; and those of sequence identification numbers 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences designated therein as, respectively, sequence identification number 1 and sequence identification number 7); 5D (having light chain variable and heavy chain variable sequences designated therein as, respectively, sequence identification number 2 and sequence identification number 9); 2H (having light chain variable and heavy chain variable sequences designated therein as, respectively, sequence identification number 3 and sequence identification number 10); 43H (having light chain variable and heavy chain variable sequences designated therein as, respectively, sequence identification number 6 and sequence identification number 14); 41H (having light chain variable and heavy chain variable sequences designated therein as, respectively, sequence identification number 5 and sequence identification number 13); and 15H (having light chain variable and heavy chain variable sequences designated therein as, respectively, sequence identification number 4 and sequence identification number 12), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number 17 and the light chain of sequence identification number 18; those having the heavy chain variable region of sequence identification number 6 and the light chain variable region of sequence identification number 8; those having the heavy chain of sequence identification number 19 and the light chain of sequence identification number 20; those having the heavy chain variable region of sequence identification number 10 and the light chain variable region of sequence identification number 12; those having the heavy chain of sequence identification number 32 and the light chain of sequence identification number 20; those having the heavy chain variable region of sequence identification number 30 and the light chain variable region of sequence identification number 12; those having the heavy chain sequence of sequence identification number 21 and the light chain sequence of sequence identification number 22; those having the heavy chain variable region of sequence identification number 14 and the light chain variable region of sequence identification number 16; those having the heavy chain of sequence identification number 21 and the light chain of sequence identification number 33; and those having the heavy chain variable region of sequence identification number 14 and the light chain variable region of sequence identification number 31, as disclosed in the foregoing publication. A specific antibody contemplated is antibody 1119 as disclosed in the foregoing U.S. publication and having a complete heavy chain of sequence identification number 17 as disclosed therein and having a complete light chain of sequence identification number 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and 0A-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number 8 and a light chain variable region having sequence identification number 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); b anti-IP10 Ulcerative Colitis mAb (MDX-1100); anti-LLY antibody; BMS-66513; anti-Mannose Receptor/hCG8 mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti- VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
   a housing having an exterior surface releasably attachable to a patient;
   a fluid conduit disposed in the housing;
   a syringe disposed in the housing and including
      a reservoir containing a drug,
      a needle having a proximal end in fluid communication with the reservoir and a distal end disposed exterior to the reservoir, and
      a stopper movable through the reservoir from a proximal end of the reservoir toward a distal end of the reservoir to expel the drug from the reservoir via the needle during operation of the drug delivery device; and
   a seal member connected to the syringe, the seal member having an initial position wherein a distal end of the needle is partially disposed through the seal member and a delivery position wherein the distal end of the needle is disposed through an exterior surface of the seal member into fluid communication with the fluid conduit.

2. The drug delivery device of claim 1, the seal member being made of a rubber material that is permeable to at least one gaseous sterilizing agent.

3. The drug delivery device of claim 2, the at least one gaseous sterilizing agent including ethylene oxide.

4. The drug delivery device of claim 1, the syringe including a barrel surrounding at least a portion of the reservoir and a neck surrounding at least a portion of the needle, the neck having a smaller width or diameter than the barrel.

5. The drug delivery device of claim 4, at least a portion of the neck of the syringe being slidably received in a recess formed in the seal member.

6. The drug delivery device of claim 5, the seal member having an interior surface surrounding the recess and sealingly engaging an exterior surface of the neck of the syringe.

7. The drug delivery device of claim 4, comprising a first connection hub connecting the fluid conduit and the seal member.

8. The drug delivery device of claim 7, an interior surface of the first connection hub sealingly engaging a radially outwardly facing portion of the exterior surface of the seal member.

9. The drug delivery device of claim 8, a second connection hub rigidly connected to the syringe, the first connection hub being slidably received within the second connection hub.

10. The drug delivery device of claim 9, an exterior surface of the first connection hub including a first gripping element and an interior surface of the second connection hub including a second gripping element, the first gripping element frictionally engaging the second gripping element when the seal member is arranged in the initial position to limit movement of the first connection hub relative to the second connection hub.

11. The drug delivery device of claim 1, the distal end of the needle being embedded within the seal member when the seal member is arranged in the initial position.

\* \* \* \* \*